United States Patent [19]

Meals

[11] Patent Number: 5,111,808
[45] Date of Patent: May 12, 1992

[54] FOOT ELEVATOR BLANKET CRADLE

[75] Inventor: Roy A. Meals, Los Angeles, Calif.

[73] Assignee: Bissell Healthcare Corporation, Grand Rapids, Mich.

[21] Appl. No.: 619,738

[22] Filed: Nov. 29, 1990

[51] Int. Cl.⁵ ............................................. A61F 3/00
[52] U.S. Cl. ..................................... 602/23; 128/845
[58] Field of Search ............ 128/68, 69, 80 R, 84 A, 128/84 B, 84 C, 84 R, 94, 87 R, 85, 845, 849, 882; 269/322, 328; 5/443

[56] References Cited

U.S. PATENT DOCUMENTS

| | | | |
|---|---|---|---|
| 1,242,688 | 10/1917 | Hawley | 128/84 C |
| 1,366,576 | 1/1921 | Maddox | 128/85 |
| 1,768,770 | 7/1930 | Kettelkamp . | |
| 1,964,930 | 7/1934 | Siebrandt | 128/85 X |
| 2,832,334 | 4/1958 | Whitelaw . | |
| 2,911,657 | 11/1959 | Streeter | 5/444 |
| 3,066,322 | 12/1962 | Derby | 128/80 R |
| 3,256,880 | 6/1966 | Caypinar . | |
| 3,347,544 | 10/1967 | Uffenorde | 128/845 X |
| 3,472,224 | 10/1969 | Ewerwahn . | |
| 3,511,233 | 5/1970 | Holy, Jr. | 5/444 X |
| 3,848,589 | 11/1974 | Throner | 128/84 C |
| 3,878,842 | 4/1975 | Goldberg | 128/84 C |
| 4,223,669 | 9/1980 | Morledge | 128/849 X |
| 4,323,060 | 4/1982 | Pecheux | 128/84 R |
| 4,328,794 | 5/1982 | Holmes | 128/85 |
| 4,520,805 | 6/1985 | St. Vincent et al. | 128/80 R |
| 4,664,099 | 5/1987 | Pearl, Jr. | 128/84 C X |
| 4,807,609 | 2/1989 | Meals . | |
| 4,964,400 | 10/1990 | Laico et al. | 128/84 C X |
| 5,002,046 | 3/1991 | Scott | 128/84 C X |

FOREIGN PATENT DOCUMENTS

| | | | |
|---|---|---|---|
| 219785 | 7/1961 | Austria | 5/443 |
| 920448 | 4/1947 | France | 128/84 C |

OTHER PUBLICATIONS

"Healthcare Catalog", Fred Sammons, Inc., 1990 Ed., p. B31.
"Professional Healthcare Catalog", Fred Sammons, Inc., 1989 Mid-year Ed., pp. B28-B29.
"Posey Patent Safety Aids", 1988 Product Line p. 17.
"Enrichments For Better Living", Fall 1988, p. 30.

*Primary Examiner*—Richard J. Apley
*Assistant Examiner*—Linda C. M. Dvorak
*Attorney, Agent, or Firm*—Price, Heneveld, Cooper, DeWitt & Litton

[57] ABSTRACT

A foot elevator having a peripheral wire base frame releasably connected with a peripheral wire upper frame. A peripheral wire blanket support frame releasably connectable to the base and upper frames is also provided. The base frame, the upper frame and the blanket support are releasably connected for disassembly and compact storage of the device. A cradle of flexible material is provided over a portion of the upper frame for support of a patient's lower limb.

38 Claims, 2 Drawing Sheets

FOOT ELEVATOR BLANKET CRADLE

BACKGROUND OF THE INVENTION

The present invention relates to medical therapy and appliances for post operative or post injury treatment of lower limbs.

Patients recovering from surgery involving the lower limbs or after treatment of injury to the lower limbs sometimes require an elevated position for the lower limb for proper positioning and to minimize potential edema or swelling. The weight of blankets and the like, bearing upon the foot of a patient can tend to rotate the patient's leg, causing distress to such patients. Further, the patient's condition might be that bedding laid over and contacting the patient can cause trauma or injury to a treated and recovering area of the lower limb. Thus, it is often desirable to use a blanket support with the foot elevator Prior foot elevator devices have consisted of a foam block which is molded or cut to the desired contour and shape. Such foam block devices are bulky to handle and store. Alternatively, a wrap-style splint device has been used. However, such wrap-style devices are contraindicated where minimizing contact is desired.

Both prior devices restrict the circulation of air along the patient's skin where the device is used, causing irritation and general discomfort. Both prior devices are difficult to clean or sanitize for prolonged use or use by subsequent patients. Further, neither device provides satisfactory protection to the lower limb, especially the foot and toe area, from the weight and discomfort of blankets and other bedding bearing on the foot and toes.

SUMMARY OF THE INVENTION

The foot-elevator and blanket support of the present invention address the deficiencies of the prior devices. A collapsible device having an upper peripheral frame supporting a cradle is provided The upper frame is releasably connected to a base peripheral frame.

In one aspect of the invention, a peripheral frame blanket support is also releasably connected to the upper and base frames. In another aspect of the invention, the various peripheral frames are formed from stainless steel wire for enhanced durability and maintenance, including ease of sanitation. In another aspect of the invention, the cradle is a removable fabric covering which is stretched over the upper frame to form a hammock-like receiving area for the lower limb and enhances free air circulation to the body portion engaged thereby. The configuration of the wire frame is such that no body portion need contact the wire frame itself.

Further, the assembled device does not have the bulk of the prior devices. The three wire frame members can be disconnected from each other to further minimize the bulk of the present invention and enhance compact storage. When in its collapsed state, the preferred embodiment constitutes a mere fraction of the bulk of prior devices.

These and other objects, advantages and features of the present invention will become apparent upon review of the following specification in conjunction with the drawings.

DESCRIPTION OF THE PREFERRED EMBODIMENT

Figure 1:
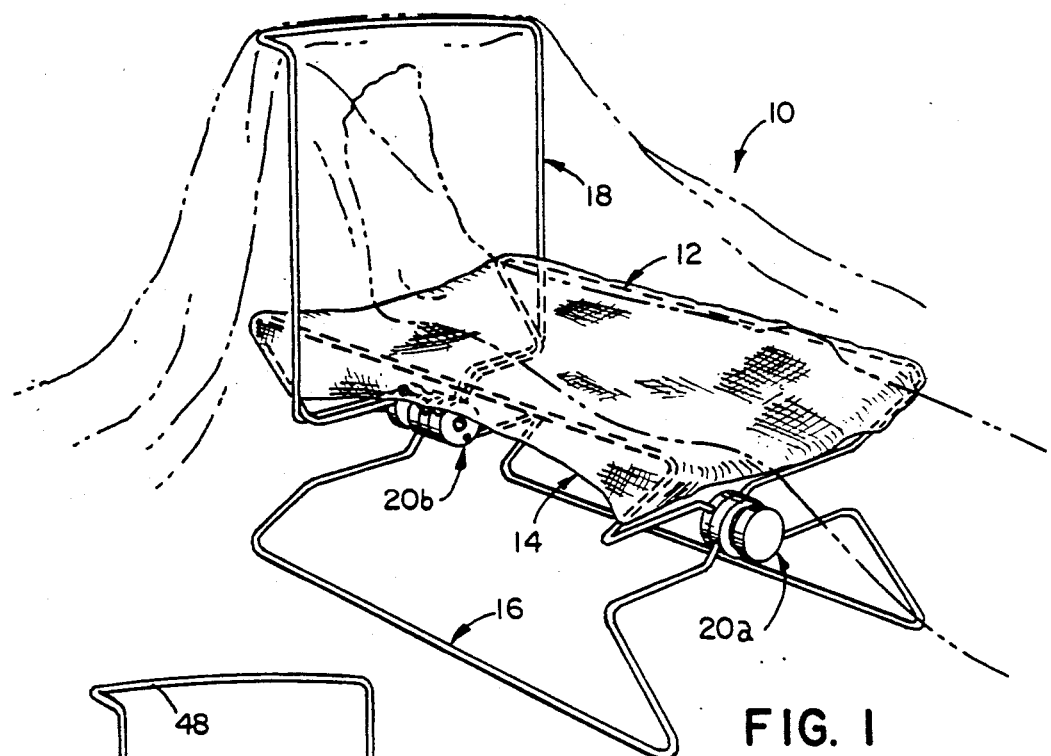
FIG. 1 is a perspective view of the invention as used by a patient, with a portion of a lower limb and a portion of typical bedding shown in phantom.

In a preferred embodiment, a foot elevator 10 of the present invention includes an upper peripheral frame 12, a cradle or hammock 14, a base peripheral frame 16 and a blanket support frame 18 (FIG. 1). Upper frame 12 and base frame 16 are releasably connected at the proximal and distal ends of foot elevator 10 by releasable connector mechanisms 20a and 20b. At the distal end of foot elevator 10, blanket support 18 releasably engages connecting mechanism 20b.

Figure 2:
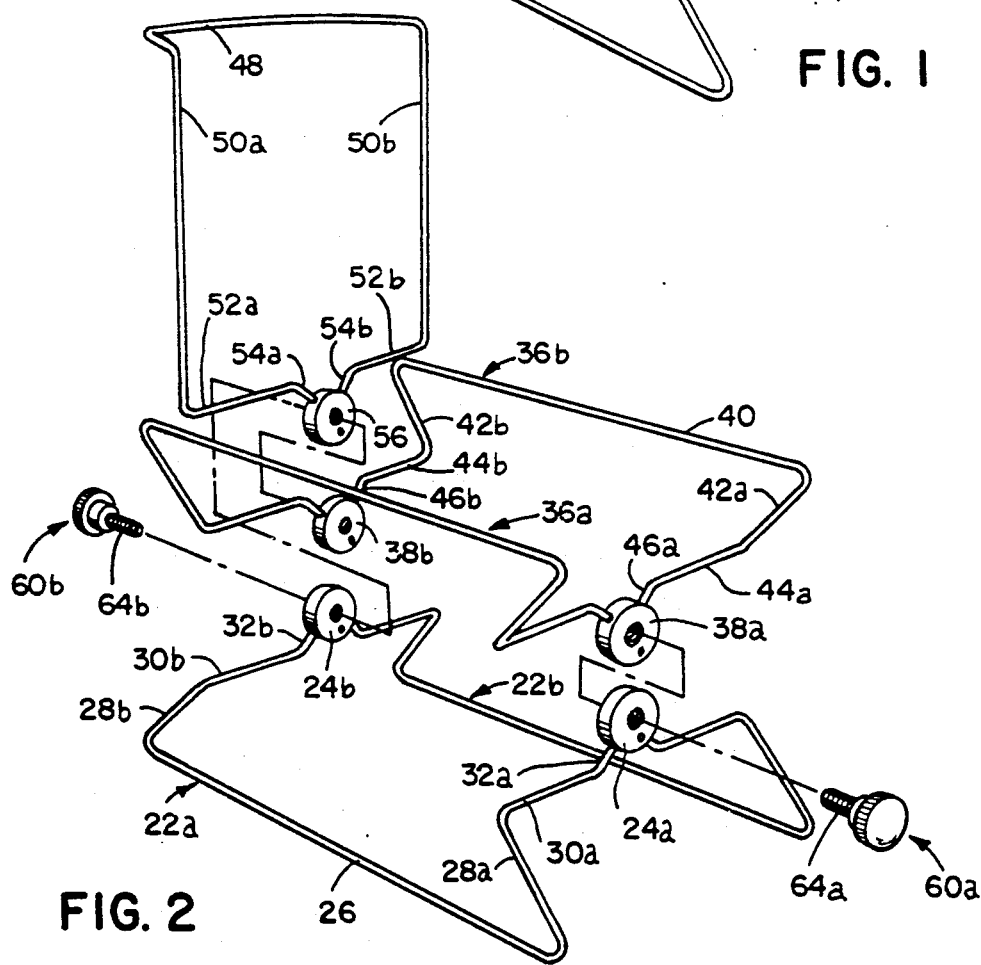
FIG. 2 is an exploded perspective view of the invention.

Base frame 16 comprises two frame members 22a and 22b and two connector disks 24a and 24b (FIG. 2). Each frame member 22 has a linear midportion 26, a pair of legs 28a and 28a, a pair of lateral portions 30a and 30b and terminal ends 32a and 32b. Each frame member 22 is preferably bent from approximately 0.187 inch (4.75 mm) diameter stainless steel wire. Legs 28 extend generally upwardly and inwardly, toward each other, from the ends of midportion 26. Legs 28 and midportion 26 lie substantially within a generally vertical reference plane. An approximately forty-five degree angle is defined between midportion 26 and each leg 28a and 28b. Lateral portions 30 extend generally horizontally and perpendicularly from legs 28. Terminal ends 32 extend approximately forty-five degrees upwardly and outwardly, away from midportion 26 at the end of lateral portions 30 and connect with connector disks 24.

Upper peripheral frame 12 is quite similar to base frame 16, having frame members 36a and 36b and connector disks 38a and 38b (FIG. 2). As with frame members 22 frame members 36 have a linear midportion 40, a pair of legs 42a and 42b, a pair of lateral portions 44a and 44b and terminal ends 46a and 46b. Each frame member 36 is also preferably bent from approximately 0.187 inch (4.75 mm) diameter stainless steel wire. Legs 42 extend generally downwardly and inwardly, toward each other, from each end of midportion 40. Legs 42 and midportion 40 lie substantially within a generally vertical reference plane. An approximately forty-five degree angle is defined between midportion 40 and each leg 42a and 42b. Lateral portions 44 extend generally horizontally and perpendicularly from legs 42. Terminal ends 46 extend approximately forty-five degrees outwardly and downwardly, away from midportion 40, from the end of lateral portions 44 and connect with connector disks 38. For manufacturing simplicity, each frame member 22 and 36 is preferably identical.

Blanket support 18 comprises a generally semicircular midportion 48, legs 50a and 50b, lateral portions 52a and 52b, terminal ends 54a and 54b and connector disk 56 (FIG. 2). Semicircular midportion 48 lies generally horizontally with legs 50 descending generally vertically from each end of midportion 48. Lateral portions 52 extend generally horizontally and perpendicularly toward each other from the lower end of legs 50. Terminal ends 54 extend approximately forty-five degrees downwardly and toward each other from the ends of lateral portions 52 and connect with connector disk 56.

Figure 3:
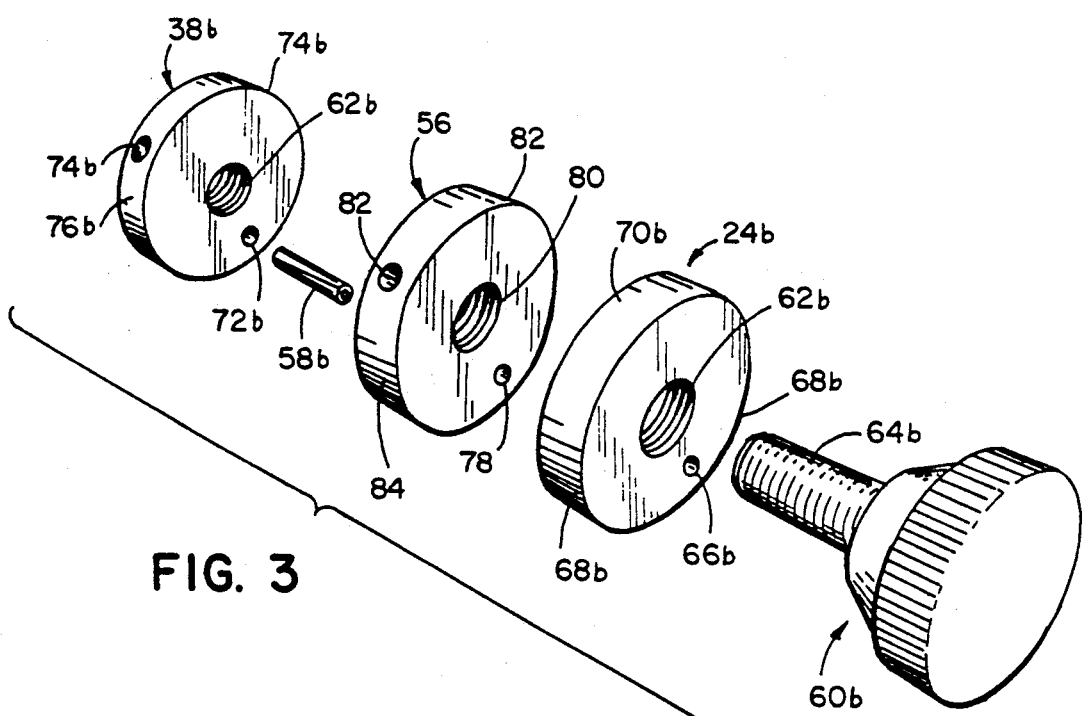
FIG. 3 is an exploded perspective detail view of the connecting device at the distal end of the invention.
Figure 4:
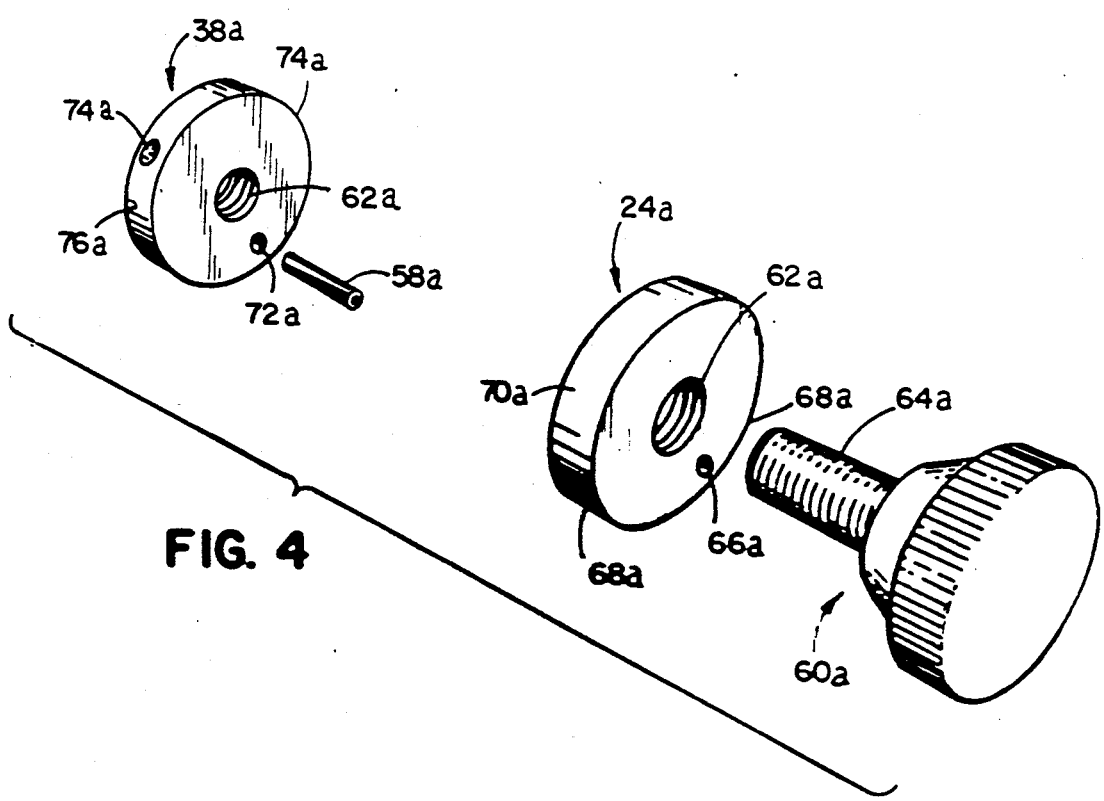
FIG. 4 is an exploded perspective detail view of the connecting device at the proximal end of the invention.

Releasable connectors 20a and 20b comprise connector disks 24a and 24b, connector disks 38a and 38b, indexing pins 58a and 58b and handscrews 60a and 60b (FIGS. 3 and 4). Each disk 24 and 38 is preferably aluminum, approximately 1.375 inch (34.9 mm) in diameter and 0.25 inch (6.35 mm) thick. Each disk 24 and 38 also has a threaded aperture 62 for receiving the threaded shaft 64 of handscrew 60. By reference to the positions on a clockface, disk 24 is also provided with an indexing pin aperture 66 at the 5:30 position for forcibly receiving pin 58 and has a pair of frame apertures 68 penetrating the edge 70 of disk 24 at the 4:30 and 7:30 clock positions. Terminal ends 32 of base frame 16 are forcibly fit into frame apertures 68 (FIG. 2).

Disk 38 has an indexing pin aperture 72 at the 5:30 position (FIGS. 3 and 4). However, aperture 72 is sized for a slip fit with pin 58. Disk 38 also has a pair of frame apertures 74 at the 10:30 and 1:30 clock positions which penetrate the edge 76 of disk 38. Terminal ends 46 of upper frame 12 are forcibly fit into frame apertures 74 (FIG. 2).

Connector disk 56 is identical to disk 38 having an indexing pin aperture 78 for slip fit engagement with pin 58, a threaded aperture 80 for receiving threaded shaft 64 of handscrew 60 and a pair of frame apertures 82, positioned at the 10:30 and 1:30 clock positions and penetrating the edge 84 of disk 56 (FIG. 3). Terminal ends 54 of support frame 18 are forcibly fit into frame apertures 82 (FIG. 2).

Cradle 14 is constructed from a flexible material, preferably a knit-cotton blend as is commonly found in athletic socks and the like (FIG. 1). Cradle 14 is fabricated in a sock-like fashion to form a fabric tube with two open ends. The resulting "sock" is simply slid over upper frame 12 in a sock-like manner to assemble cradle 14 to upper frame 12 at midportion 40 of members 36. The "sock" breathes freely and allows free air circulation to the body part which is in contact with the "sock."

In use, upper frame 12 and base frame 16 are assembled as indicated in FIG. 2. Support frame 18 might or might not be included, depending upon the specific indications for treatment. Indexing pins 58 of disks 24 are aligned with pin apertures 72 of disks 38 and pin aperture 78 of disk 56, if support frame 18 is included (FIG. 3). Threaded shafts 64 of handscrews 60 are screwed into threaded apertures 62 and 80 to securely fasten frames 12, 16 and 18 together (FIGS. 1, 2, 3, and 4).

Foot elevator 10 can easily be cleaned and sanitized by removing cradle 14 from upper frame 12. Cradle 14 may be easily laundered or replaced and each frame 12, 16 and 18 and connector 20 can be sanitized using standard methods.

The above description is considered that of the preferred embodiment only. Modifications of the invention will occur to those who make or use the invention. Therefore, it is understood that the embodiment shown in the drawings and described above is merely for illustrative purposes and is not intended to limit the scope of the invention which is defined by the following claims as interpreted according to the principals of patent law.

The embodiments of the invention in which an exclusive property or privilege is claimed are defined as follows:

1. A collapsible foot elevator comprising:
   an upper peripheral frame defining a cradle support area and having distal and proximal ends;
   cradle means connected with the upper frame at the cradle support area;
   a base peripheral frame defining a supporting base for the upper peripheral frame and having distal and proximal ends; and
   releasable attachment means at each end of each frame for releasably attaching the distal ends together in a predetermined position relative to one another and releasably attaching the proximal ends together in a predetermined position relative to one another.

2. The foot elevator of claim 1 wherein the upper frame and the base frame are each defined by at least a single, continuous length, elongated member.

3. The foot elevator of claim 2 wherein the upper frame and the base frame are each defined by two, continuous lengths of approximately 0.187 inch diameter stainless steel wire.

4. The foot elevator of claim 1 wherein each attachment means has first and second cooperating connector members, the first connector member of each attachment means is attached to the upper frame, the second connector member of each attachment means is attached to the base frame and the first and second connector members of each attachment means are adapted to releasably interconnect with each other for positioning the upper frame and base frame relative to each other.

5. The foot elevator of claim 4 wherein the first connector member has a surface, the second connector member has a surface and the two surfaces are adapted to abut each other and index the relative position of the upper frame and the base frame.

6. The foot elevator of claim 5 wherein each attachment means further includes an indexing pin, the first connector member has an aperture for receiving the indexing pin, the second connector member has an aperture aligned with the aperture of the first connector member for receiving the indexing pin and the indexing pin engages both apertures.

7. The foot elevator of claim 6 wherein each attachment means further includes a handscrew, the first connector member has an aperture for receiving the handscrew, the second connector member has an aperture aligned with the aperture of the first connector member for receiving the handscrew, at least one of the apertures for receiving the handscrew is threaded and the handscrew engages the apertures for fastening the connector members together.

8. The foot elevator of claim 7 wherein the connector members are similarly sized and shaped aluminum disks and each disk is approximately 0.25 inch thick and approximately 1.375 inch in diameter.

9. The foot elevator of claim 5 further including a blanket support, having an upper end and a lower end.

10. The foot elevator of claim 9 wherein the blanket support is a peripheral frame formed of a single, continuous elongated member.

11. The foot elevator of claim 10 wherein the single, continuous elongated member is approximately 0.187 inch diameter stainless steel wire.

12. The foot elevator of claim 11 wherein the blanket support further includes a third connector member at the lower end and the third connector member is adapted for cooperating engagement with the first and second connector members at the distal ends of the upper frame and the base frame, respectively, for positioning the blanket support relative to the upper frame and the lower frame.

13. The foot elevator of claim 12 wherein the third connector member has a first surface adapted to abut the surface of the first connector member, attached to the distal end of the upper frame, for indexing the relative position of the blanket support and the upper frame and a second surface adapted to abut the surface of the second connector member, attached to the distal end of the base frame, for indexing the relative position of the blanket support and the base frame.

14. The foot elevator of claim 13 wherein each attachment means further includes an indexing pin, the first connector member has an aperture for receiving the indexing pin, the second connector member has an aperture aligned with the aperture of the first connector member for receiving the indexing pin, the third connector member has an aperture aligned with the apertures in the first and second connector members at the distal ends of the upper and base frames, respectively, for receiving the indexing pin and the indexing pin engages the apertures.

15. The foot elevator of claim 14 wherein each attachment means further includes a handscrew, the first connector member has an aperture for receiving the handscrew, the second connector member has an aperture aligned with the aperture of the first connector member for receiving the handscrew, the third connector member has an aperture aligned with the apertures of the first and second connector members at the distal ends of the upper and base frames, respectively, for receiving the handscrew, at least one of the apertures is threaded and the handscrew engages the apertures for fastening the connector members together.

16. The foot elevator of claim 15 wherein the first, second and third connector members are similarly sized and shaped aluminum disks and each disk is approximately 0.25 inch thick and 1.375 inch diameter.

17. The foot elevator of claim 13 wherein the cradle means is a flexible material suspended at the cradle support area of the upper frame.

18. The foot elevator of claim 17 wherein the flexible material is fabricated in a sock-like fashion to form a fabric tube with two open opposing ends.

19. A collapsible foot elevator comprising:
an upper peripheral frame defining a cradle support area and having distal and proximal ends;
cradle means connected with the upper frame at the cradle support area;
a base peripheral frame defining a supporting base for the upper peripheral frame and having distal and proximal ends;
a blanket support peripheral frame having a lower end; and
releasable attachment means at each of the distal and proximal ends of each of the upper and base frames and at the lower end of the blanket support frame for releasably attaching the upper frame distal end, base frame distal end and blanket support frame lower end together in a predetermined position relative to one another and releasably attaching the upper and base frame proximal ends together in a predetermined position relative to one another.

20. The foot elevator of claim 19 wherein each frame is defined by at least a single, continuously elongated member.

21. The foot elevator of claim 20 wherein the upper frame and the base frame are each defined by two continuous lengths of wire, the blanket support frame is defined by a single continuous length of wire and the wire is approximately 0.187 inch diameter stainless steel wire.

22. The foot elevator of claim 20 wherein each attachment means has first and second cooperating connector members, the first connector member of each attachment means is attached to the upper frame, the second connector member of each attachment means is attached to the base frame and the first and second connector members of each attachment means are adapted to releasably interconnect with each other for positioning the upper frame and base frame relative to each other.

23. The foot elevator of claim 22 wherein the attachment means at the distal end of the foot elevator further includes a third connector member at the lower end of the blanket support frame and the third connector member is adapted for cooperating engagement with the first and second connector members at the distal end of the upper frame and the base frame, respectively, for positioning the blanket support relative to the upper frame and the lower frame.

24. The foot elevator of claim 23 wherein the first connector member has a surface, the second connector member has a surface and the two surfaces are adapted to abut each other and index the relative position of the upper frame and the base frame.

25. The foot elevator of claim 24 wherein the third connector member has a first surface adapted to abut the surface of the first connector member, attached to the distal end of the upper frame, for indexing the relative position of the blanket support frame and the upper frame and a second surface adapted to abut the surface of the second connector member, attached to the distal end of the base frame, for indexing the relative position of the blanket support and the base frame.

26. The foot elevator of claim 25 wherein each attachment means further includes an indexing pin, the first connector member has an aperture for receiving the indexing pin, the second connector member has an aperture aligned with the aperture of the first connector member for receiving the indexing pin, the third connector member has an aperture aligned with the apertures in the first and second connector members at the distal ends of the upper and base frames, respectively, for receiving the indexing pin and the indexing pin engages the apertures.

27. The foot elevator of claim 26 wherein each attachment means further includes a handscrew, the first connector member has an aperture for receiving the handscrew, the second connector member has an aperture aligned with the aperture of the first connector members for receiving the handscrew, the third connector member has an aperture aligned with the apertures of the first and second connector members at the distal ends of the upper and base frames, respectively, for receiving the handscrew, at least one of the apertures is threaded and the handscrew engages the apertures for fastening the connector members together.

28. The foot elevator of claim 27 wherein the first, second and third attachment members are similarly sized and shaped aluminum disks and each disk is approximately 0.25 inch thick and 1.375 inch diameter.

29. The foot elevator of claim 25 wherein the cradle means is a flexible material suspended at the cradle support area of the upper frame.

30. The foot elevator of claim 29 wherein the flexible material is fabricated in a sock-like fashion to form a fabric tube with two open opposing ends.

31. The foot elevator of claim 30 wherein the flexible material is a knit-cotton blend.

32. A collapsible foot elevator comprising:
 a first wire frame having proximal and distal ends and being removably secured to and above a second wire frame, the second frame having proximal and distal ends and being designed to rest on a mattress or other support surface;
 a cradle removably secured to the first frame, the cradle supporting at least a foot portion of a patient above the mattress or other support surface;
 a first attachment means detachably connecting the distal ends of the first and second frames in a predetermined position relative to one another; and
 a second attachment means detachably connecting the proximal ends of the first and second frames in a predetermined position relative to one another.

33. The foot elevator of claim 32 wherein each attachment means has first and second cooperating connector members, the first connector member of each attachment means is attached to the first frame, the second connector member of each attachment means is attached to the second frame and the first and second connector members of each attachment means are adapted to releasably interconnect with each other for positioning the first frame and second frame relative to each other.

34. The foot elevator of claim 33 further including a third wire frame member having a lower end and removably supported by the second frame above the first frame to elevate a blanket or other cover above and spaced from a foot supported by the cradle.

35. The foot elevator of claim 34 wherein the third frame member has a third connector member attached to its lower end and the third connector member is adapted to engage and cooperate with at least one of the first and second attachment means for positioning the third frame member relative to the first and second frame members.

36. The foot elevator of claim 35 wherein each attachment means further includes an indexing pin, each of the connector members has an aperture for receiving the indexing pin, the apertures align, one with another, and the indexing pin engages the apertures.

37. The foot elevator of claim 36 wherein each attachment means further includes a handscrew, each connector member has an aperture for receiving the handscrew, each aperture aligns, one with another, at least one of the apertures is threaded and the handscrew engages the apertures for fastening the connector members together.

38. The foot elevator of claim 32 wherein the cradle is a breathable fabric forming a sock having two open ends and which is removably mounted over the first wire frame.

* * * * *

UNITED STATES PATENT AND TRADEMARK OFFICE
CERTIFICATE OF CORRECTION

PATENT NO. : 5,111,808
DATED      : May 12, 1992
INVENTOR(S) : Roy A. Meals

It is certified that error appears in the above-identified patent and that said Letters Patent is hereby corrected as shown below:

Column 1, line 42:
　　After "provided" insert --.--.

Column 2, line 27:
　　"legs 28a and 28a," should be --legs 28a and 28b,--.

Signed and Sealed this

Nineteenth Day of October, 1993

Attest:

BRUCE LEHMAN

Attesting Officer    Commissioner of Patents and Trademarks